(12) United States Patent
King (10) Patent No.: US 9,593,969 B2
(45) Date of Patent: Mar. 14, 2017

(54) CONCEALED ELECTRICAL CONNECTORS

(71) Applicant: Apple Inc., Cupertino, CA (US)

(72) Inventor: Nicholas V. King, San Jose, CA (US)

(73) Assignee: Apple Inc., Cupertino, CA (US)

(*) Notice: Subject to any disclaimer, the term of this patent is extended or adjusted under 35 U.S.C. 154(b) by 170 days.

(21) Appl. No.: 14/142,641

(22) Filed: Dec. 27, 2013

(65) Prior Publication Data
US 2015/0185055 A1 Jul. 2, 2015

(51) Int. Cl.
*G01D 11/24* (2006.01)
*A61B 5/02* (2006.01)
*A61B 5/00* (2006.01)
*G06F 19/00* (2011.01)
*A61B 5/117* (2016.01)
*A61B 5/0205* (2006.01)

(52) U.S. Cl.
CPC ............ *G01D 11/245* (2013.01); *A61B 5/02* (2013.01); *A61B 5/6887* (2013.01); *A61B 5/6898* (2013.01); *G06F 19/3406* (2013.01); *A61B 5/0205* (2013.01); *A61B 5/1172* (2013.01); *A61B 2560/0462* (2013.01); *A61B 2560/0468* (2013.01); *A61B 2562/227* (2013.01)

(58) Field of Classification Search
CPC ................................. G06F 1/16; G06F 1/1626
USPC .... 361/679.3, 679.56, 679.01; 600/300, 500, 600/501, 502, 504, 506; 455/575.1–575.9
See application file for complete search history.

(56) References Cited

U.S. PATENT DOCUMENTS

| | | | |
|---|---|---|---|
| 2,798,895 | A | 7/1957 | Nowotny |
| 2,798,896 | A | 7/1957 | Bly |
| 4,152,825 | A | 5/1979 | Bruneau |
| 4,344,603 | A | 8/1982 | Hozumi |
| 4,455,026 | A | 6/1984 | Pinkus |
| 5,238,222 | A | 8/1993 | Sumida |
| 5,580,676 | A | 12/1996 | Honda et al. |
| 6,106,973 | A | 8/2000 | Sonozaki et al. |
| 6,174,164 | B1 | 1/2001 | Masjedi |
| 6,358,644 | B1 | 3/2002 | Shibata et al. |
| 6,368,744 | B1 | 4/2002 | Hatazawa et al. |
| 6,528,204 | B1 | 3/2003 | Hikmet et al. |
| 6,549,756 | B1 * | 4/2003 | Engstrom .......... A61B 5/02438 455/100 |

(Continued)

FOREIGN PATENT DOCUMENTS

| | | |
|---|---|---|
| EP | 0792741 | 2/1986 |
| EP | 1931010 | 6/2008 |

(Continued)

OTHER PUBLICATIONS

International Search Report, PCT No. PCT/US2014/067787, 12 pages, Feb. 16, 2015.

(Continued)

*Primary Examiner* — Anthony Haughton
(74) *Attorney, Agent, or Firm* — Kilpatrick Townsend & Stockton LLP (57) ABSTRACT

An electronic device with a rigid housing includes multiple apertures which each define a portion of a symbol used to identify the device. Conducting inserts may be positioned within the apertures to provide externally-accessible electrical connectors. The electrical connector may be used as a portion of a sensor or a charging circuit.

20 Claims, 7 Drawing Sheets

(56) References Cited

U.S. PATENT DOCUMENTS

| | | | |
|---|---|---|---|
| 6,790,178 B1* | 9/2004 | Mault | A61B 5/0011 128/903 |
| 6,924,551 B2 | 8/2005 | Rumer et al. | |
| 7,103,407 B2* | 9/2006 | Hjelt | A61B 5/0537 600/547 |
| 7,270,910 B2 | 9/2007 | Yahnker et al. | |
| 7,288,340 B2 | 10/2007 | Iwamoto | |
| 7,356,923 B2 | 4/2008 | Honer | |
| 7,622,895 B1 | 11/2009 | Griffin | |
| 7,663,064 B2 | 2/2010 | Dutta et al. | |
| 7,714,542 B2 | 5/2010 | Lee et al. | |
| 7,887,948 B2 | 2/2011 | Jang et al. | |
| 7,910,243 B2 | 3/2011 | Koh et al. | |
| 7,972,721 B2 | 7/2011 | Kozu et al. | |
| 7,976,981 B2 | 7/2011 | Lee | |
| 8,031,122 B2 | 10/2011 | Jang et al. | |
| 8,034,477 B2 | 10/2011 | Yamada | |
| 8,119,278 B2 | 2/2012 | Bailey et al. | |
| 8,124,269 B2 | 2/2012 | Takahashi et al. | |
| 8,241,786 B2 | 8/2012 | Taniguchi et al. | |
| 8,259,013 B2 | 9/2012 | Jang et al. | |
| 8,260,371 B2 | 9/2012 | Kawata et al. | |
| 8,293,402 B2 | 10/2012 | Lee | |
| 8,427,825 B2* | 4/2013 | Szczypinski | H04M 1/0262 29/592.1 |
| 8,445,125 B2 | 5/2013 | Baek et al. | |
| 8,518,569 B2 | 8/2013 | Murphy et al. | |
| 8,526,998 B2* | 9/2013 | Koide | A61B 5/02438 455/550.1 |
| 8,558,509 B2 | 10/2013 | He et al. | |
| 8,603,670 B2 | 12/2013 | Taniguchi et al. | |
| 8,778,529 B2 | 7/2014 | Seo | |
| 8,942,409 B2 | 1/2015 | Kantor et al. | |
| 8,999,566 B2 | 4/2015 | Chung et al. | |
| 2003/0129483 A1 | 7/2003 | Gross | |
| 2005/0142439 A1 | 6/2005 | Lee et al. | |
| 2007/0154794 A1 | 7/2007 | Kim et al. | |
| 2007/0260136 A1 | 11/2007 | Hunter | |
| 2007/0264535 A1 | 11/2007 | Lee et al. | |
| 2008/0001573 A1 | 1/2008 | Carey | |
| 2008/0286644 A1 | 11/2008 | Yeo | |
| 2009/0246620 A1 | 10/2009 | Lee et al. | |
| 2009/0317708 A1 | 12/2009 | Brandl et al. | |
| 2010/0052603 A1 | 3/2010 | Bourilkov et al. | |
| 2010/0081049 A1 | 4/2010 | Holl et al. | |
| 2010/0316911 A1 | 12/2010 | Tesson et al. | |
| 2011/0014954 A1* | 1/2011 | Dossas | A61B 5/0002 455/566 |
| 2011/0043309 A1 | 2/2011 | Wamala et al. | |
| 2011/0076550 A1 | 3/2011 | Liang et al. | |
| 2011/0175569 A1 | 7/2011 | Austin | |
| 2011/0215480 A1 | 9/2011 | Gorczyca et al. | |
| 2011/0223447 A1 | 9/2011 | Ignor et al. | |
| 2011/0236727 A1 | 9/2011 | Jang | |
| 2011/0287318 A1 | 11/2011 | Loveness et al. | |
| 2012/0092819 A1* | 4/2012 | Szczypinski | G06F 1/1632 361/679.02 |
| 2012/0116176 A1* | 5/2012 | Moravec | A61B 5/6898 600/300 |
| 2012/0121944 A1 | 5/2012 | Yamamoto et al. | |
| 2012/0305605 A1 | 12/2012 | Vassaux et al. | |
| 2013/0034763 A1 | 2/2013 | Byun | |
| 2013/0053110 A1 | 2/2013 | Pope et al. | |
| 2013/0071696 A1 | 3/2013 | Kim et al. | |
| 2013/0171490 A1 | 7/2013 | Rothkopf et al. | |
| 2013/0323055 A1 | 12/2013 | Eden et al. | |
| 2014/0050948 A1 | 2/2014 | Hashimoto et al. | |
| 2014/0065474 A1 | 3/2014 | Werner et al. | |
| 2014/0147703 A1 | 5/2014 | Werner et al. | |
| 2014/0147730 A1 | 5/2014 | Werner | |
| 2015/0043156 A1* | 2/2015 | Jain | G06F 1/206 361/679.46 |
| 2015/0220109 A1* | 8/2015 | von Badinski | G06F 1/16 340/539.12 |
| 2015/0255776 A1 | 9/2015 | Dabov | |
| 2015/0256007 A1 | 9/2015 | Zadesky et al. | |

FOREIGN PATENT DOCUMENTS

| | | |
|---|---|---|
| EP | 2540221 | 1/2013 |
| EP | 2653053 | 10/2013 |
| JP | 61032951 | 2/1986 |
| JP | 63314770 | 12/1988 |
| JP | 10012200 | 1/1998 |
| JP | 2000058018 | 2/2000 |
| JP | 2001118547 | 4/2001 |
| JP | 2001250515 | 9/2001 |
| JP | 2001250516 | 9/2001 |
| JP | 2001332752 | 11/2001 |
| JP | 2005108750 | 4/2005 |
| JP | 2005129260 | 5/2005 |
| JP | 2005268138 | 9/2005 |
| JP | 2007048725 | 2/2007 |
| JP | 2007165200 | 6/2007 |
| JP | 2010021074 | 1/2010 |
| KR | 20010007769 | 2/2005 |
| KR | 20090075396 | 7/2009 |
| WO | WO00/41252 | 7/2000 |
| WO | WO2008/023199 | 2/2008 |
| WO | WO2011/000239 | 1/2011 |
| WO | WO2011/095758 | 8/2011 |

OTHER PUBLICATIONS

U.S. Appl. No. 13/599,377, filed Aug. 30, 2012, pending.
U.S. Appl. No. 13/685,051, filed Nov. 28, 2012, pending.
U.S. Appl. No. 13/687,698, filed Nov. 30, 2012, pending.

* cited by examiner

CONCEALED ELECTRICAL CONNECTORS

TECHNICAL FIELD

Embodiments described herein relate generally to connectors, and more particularly, to a connector concealed by a product logo provided on the housing of an electronic device.

BACKGROUND

Many electronic devices may include electrical connectors to electrically couple the electronic device to an external circuit. For example, some electronic devices may include electrical contacts which may be positioned to align with corresponding contacts of a charging station or dock. Other electronic devices may include electrical connectors as a portion of a sensor. For example, adjacent electrical connectors may complete an electrical circuit when a device may be immersed in a conductive liquid. In another example, a sensor may include certain electrical contacts as biometric sensors to measure fingerprints, heart rate, or skin conductance.

Generally, multiple connectors may be required to include multiple sensors in an electronic device. In some examples, each connector of each sensor may require an aperture within the housing of the electronic device to expose the connector. Such apertures may weaken the structural integrity of the housing, increase production complexity and cost, and may be inefficient with respect to component layout within the electronic device. These limitations may be especially problematic for small form factor electronic devices.

Accordingly, there may be a present need for an electrical connector that does not require additional apertures in the housing of an electronic device.

SUMMARY

Embodiments described herein may relate to or take the form of an electronic device with a rigid housing that may include first aperture which defines a first portion of a symbol. In some embodiments, the symbol may be a portion of a product logo or, in other embodiments the symbol may include at least a portion of a glyph. Other embodiments may include a symbol that may be a portion of a word. The first and second insert may be a letter, a portion of a letter, a counter of a letter (e.g., a region enclosed within the boundaries of a letter), or more than one letter within the word.

The aperture forming part of the symbol may be in a back, front, side or other portion of the rigid housing of the electronic device. The symbol may be a product logo, a word or phrase, a glyph or letter, or any other symbol. The electronic device may also include a second aperture that defines a second portion of the same symbol or a different symbol. The electronic device may also include a first insert portion positioned and sized to fit within the first aperture. Similarly, there may be a second insert positioned and sized to fit within the second aperture. Each of the inserts may be made from the same or different electrically conductive materials. In some embodiments, the inserts may be electrically insulated from the rigid housing. In other embodiments, the inserts may be electrically insulating and the housing may be electrically conductive.

In some embodiments, the first insert and second inserts may at least partially define an electrical path which may constitute a skin conductivity sensor, a heart rate monitor, or any other suitable biometric sensor. In further embodiments, the first and second inserts may at least partially define an electrical path constituting a battery charging circuit. In some examples, the first and second insert may be the same size. In other examples, the first and second inserts maybe sized differently.

BRIEF DESCRIPTION OF THE FIGURES

Reference will now be made to representative embodiments illustrated in the accompanying figures. It should be understood that the following descriptions are not intended to limit the embodiments to one preferred embodiment. To the contrary, it is intended to cover alternatives, modifications, and equivalents as may be included within the spirit and scope of the described embodiments as defined by the appended claims.

The use of the same or similar reference numerals in different figures indicates similar, related, or identical items.

DETAILED DESCRIPTION

Embodiments discussed herein may take the form of a connector or pair of connectors for providing an electrical contact within an aperture forming at least a portion of a product logo or other symbol in the housing of an electronic device.

The housing of the electronic device may be rigid with one or more apertures defined therein. The apertures may collectively define a symbol, glyph, word, or may take another configuration, and need not extend entirely through the housing. Inserts may be positioned within the apertures. The inserts may fill or otherwise substantially occupy the apertures in a manner to provide contrast with the housing in order to enhance the visibility of the symbol.

In some embodiments, the insert portions may be electrically conductive, defining a portion of an electrical path that includes an electrical circuit. As one non-limiting example, the electrical circuit may be a sensor. For example, the circuit may be a biometric sensor such as a fingerprint or skin conductance sensor. In other examples, the circuit may be a heart rate monitor, or other sensor configured to sense a health parameter of a person holding or otherwise contacting the device. In still further examples, the circuit may be a charging circuit for replenishing the charge of a battery within the electronic device.

In some embodiments, the insert portions may be electrically insulating, defining an insulated area of the housing which may form a portion of an electrical path as described above. For example, a symbol may include a counter portion of a glyph. In such a case, the insert portion may occupy the area defining the glyph, and the housing may occupy the area defining the counter. For a specific example, a housing may have an aperture that takes the shape of a ring, such as a glyph of the English letter O. The central portion of the ring may be formed of the same material as the housing, and an insert portion of an insulating material may occupy the area of the ring itself. In this manner, the insert portion may electrically insulate the counter portion from the rest of the housing.

In many embodiments, a symbol may have more than one portion or region, each of which may define at least one electrical contact as described herein. For example, if a symbol taking the shape of the English word "Phone" is present on the housing of an electronic device, one embodiment may include five distinct contacts, each formed as, or positioned beneath, the individual letters of the word. In another embodiment using the same word, three distinct contacts may be formed from the counters within the letters P, o and e. In still further embodiments using the same word, eight distinct contacts may be formed, five associated with the letters, and three associated with the counters. In such a case, the counter portions and the letter portions may be electrically insulated from one another with a seal, wall, or other insulating structure.

In other examples, the symbol may not take the shape of a letter of glyph, but may instead take the shape of a symbol such as a product logo, character representing a word, concept, or the like, or other design.

In some embodiments, the insert portions or the housing may be made from an electrically conductive material such as metal. In some cases, however, the electrically conductive portions may be made of electrically insulating materials which have been doped with conductive materials to increase their electrical conductivity.

In still further embodiments, the insert portions may serve multiple purposes beyond concealment and/or identification. For example, one insert portion may be at least partially optically transparent or transparent to certain electromagnetic wavelengths while being visually opaque. In this manner, an optical sensor, such as an infrared sensor, may be positioned thereunder and sense through the insert. In still further embodiments, the insert portions may function as radio frequency windows. In such a case, the insert portions may be constructed of a material that is transparent to radio frequencies of a particular band.

In further embodiments, an individual insert portion may be constructed of multiple materials such that distinct areas of the insert portion may serve different purposes. For example, a portion of an insert may be electrically conductive, and another portion of the same insert may be electrically insulating. In other examples, the insert portions may be sealed to the housing in a water-tight manner.

The materials selected for the insert portions and the rigid housing may vary from embodiment to embodiment.

Figure 1:
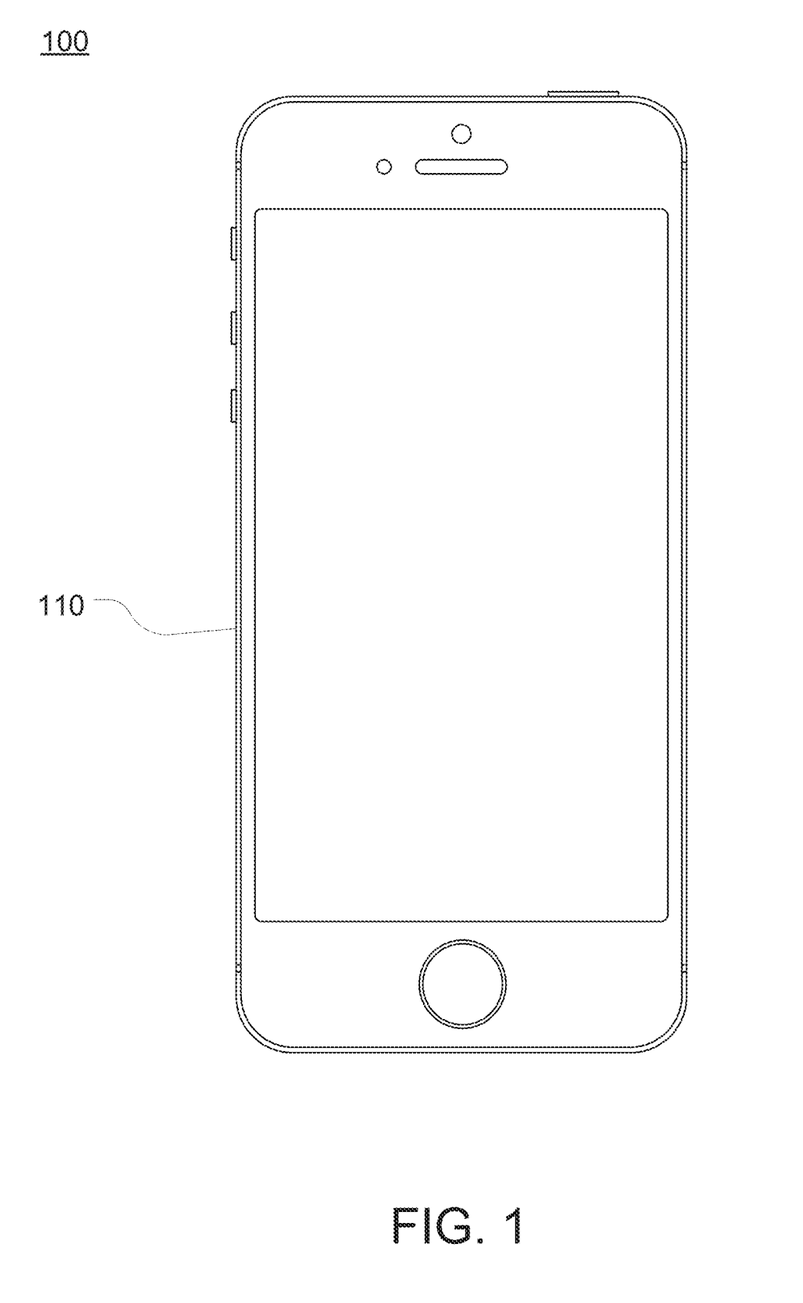
FIG. 1 depicts a front view of a sample electronic device.

FIG. 1 depicts a front view of a sample electronic device 100 that may include one or more of the electrical connectors concealed within a product logo or other symbol, as described here. The electronic device 100 may include a rigid housing 110. Although shown as a smart phone, the electronic device 100 may be any number of suitable devices including but not limited to, a tablet computing device, a wearable device, a portable computer, a desktop computer, an appliance, a touch screen, a media player, and so on. Many of these embodiments, and embodiments related thereto, preferably may be relatively small and portable such that the device may be easily and conveniently transported from place to place.

Figure 2:
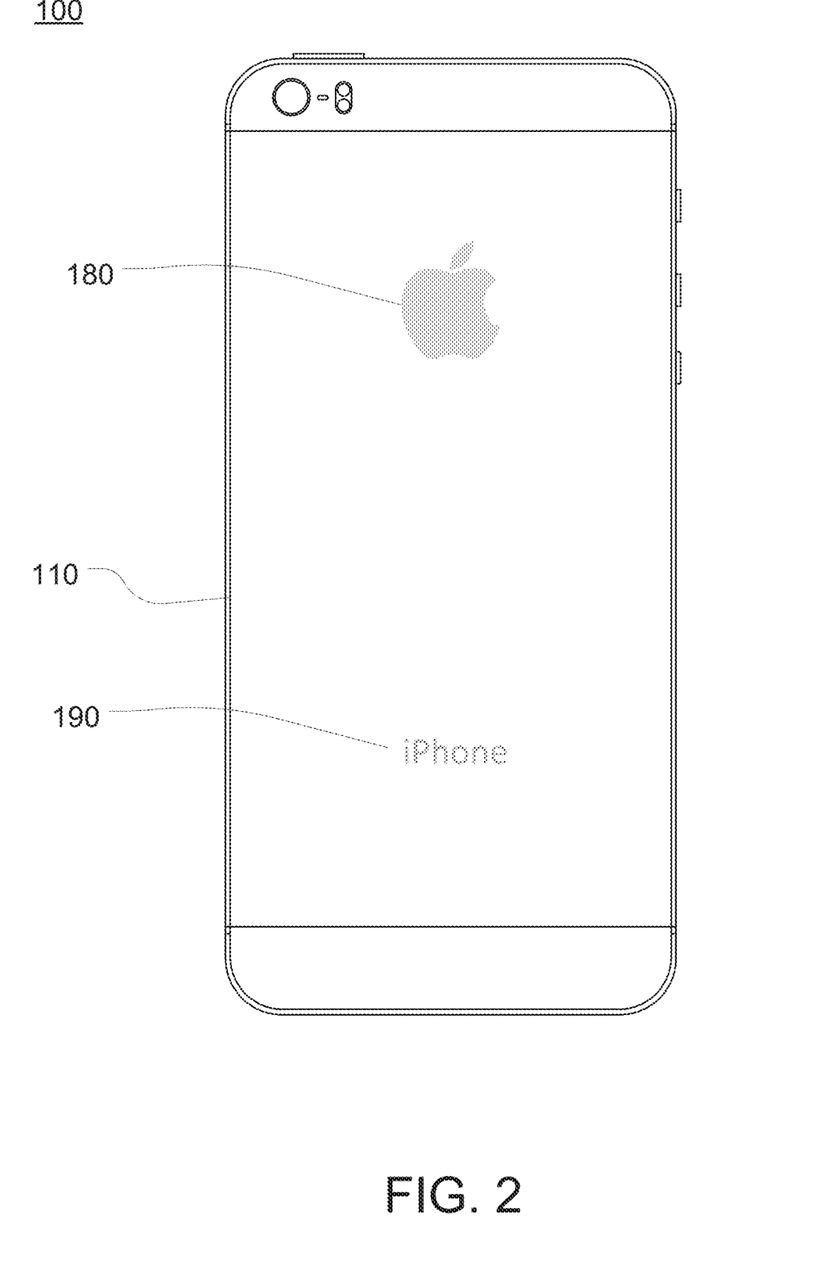
FIG. 2 depicts a back view of the sample electronic device as shown in FIG. 1.

FIG. 2 depicts a back view of the sample electronic device 100 as shown in FIG. 1. Along the back of the electronic device 100 may be one or more externally visible features that may, for example, distinguish the electronic device or provide some other visual identification. Such features may include a product logo 180 or product identifier 190, among other visual indicators. The product logo 180 may be a symbol, glyph, trademark, logo, or other symbol. The product identifier 190 may be a word or phrase to identify the model, type, or features of the electronic device 100. It should be appreciated that these are two examples of a large number of externally visible features that may be used or suitable for use with other embodiments.

In some embodiments, the product logo 180 or product identifier 190 may be positioned along the back of the housing 110, while in others they may be positioned elsewhere on a housing. In some examples the product logo 180 and/or product identifier 190 may be defined by apertures within the housing 110. For example, a housing 110 may be machined to include an aperture in the shape of the product logo 180. In a subsequent manufacturing process, an insert portion may be positioned or placed within the aperture to provide a material, texture, and contrast to the product logo 180. In this manner, the product logo 180, and the electronic device 100 may be readily identifiable.

Figure 3:
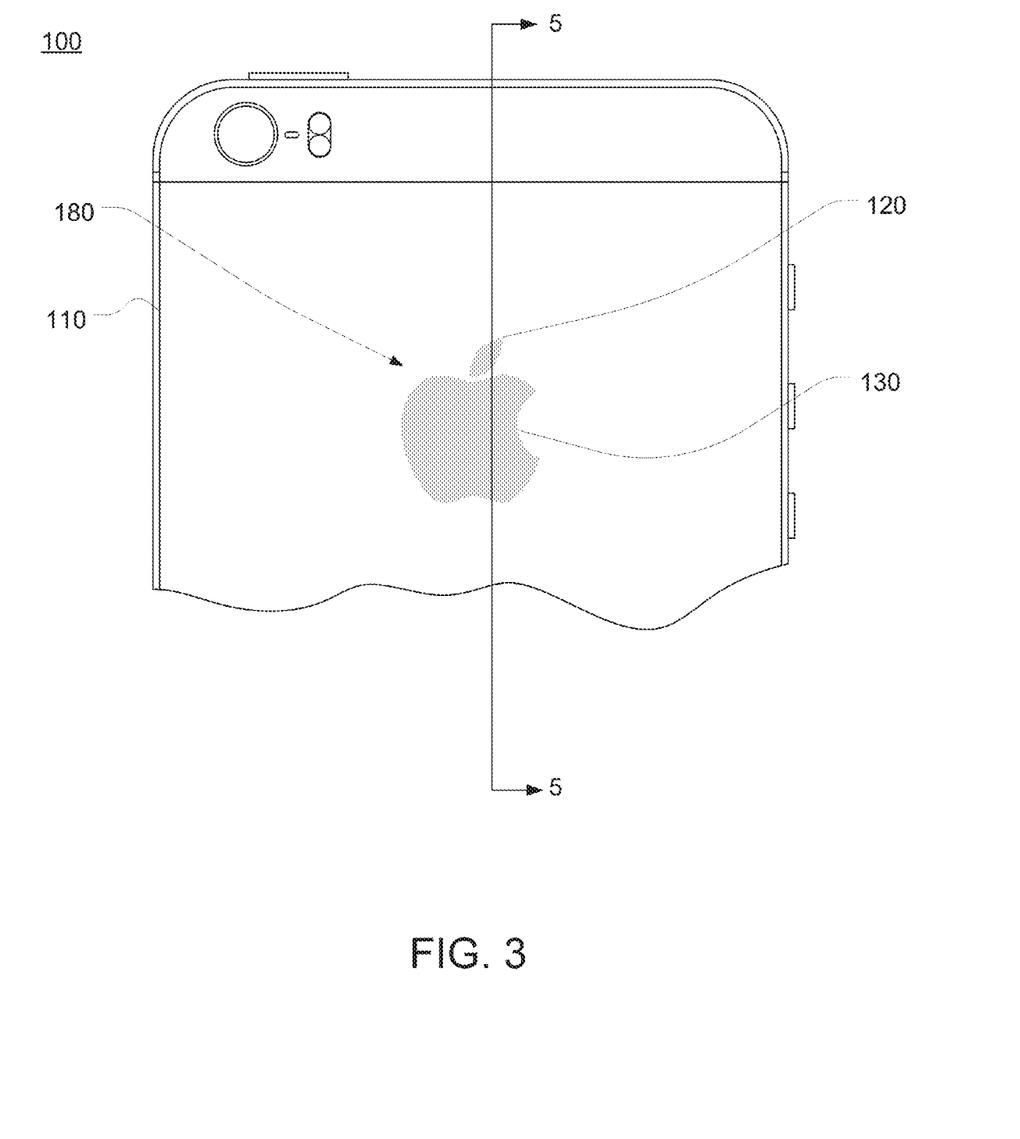
FIG. 3 depicts a detailed view of a portion of the sample electronic device shown in FIG. 2.

FIG. 3 depicts a detailed view of a portion of the sample electronic device 100 shown in FIGS. 1 and 2. FIG. 3 shows a product logo 180 having multiple distinct parts. In the illustrated embodiment, the product logo 180 may include a small insert portion 120 and an insert portion 130, each placed within a different cavity representing a different portion of the logo 180. The insert portions 120 and 130 may be composed of a material different than that of the housing 110. For example, the insert portions may be constructed of an electrically conductive material and the housing 110 may be constructed of an electrically insulating material, or vice versa. In other embodiments, the housing 110 may be electrically conductive (or nonconductive) as well as the inserts. In both housing and insert portions are electrically conductive, an insulator may be positioned between the housing 110 and each of the insert portions 120 and 130 such that none of the elements are directly electrically coupled.

In certain embodiments, the insert portions or material may completely or substantially fill the apertures in which they are positioned. The insert portions may be machined to feel smooth or contiguous with the rest of the housing, or vice versa. The insert portions may be polished, ground, lapped, or the like; such operations may be performed solely on the insert portions or solely on the housing, or may be performed on both.

Each of the logo portions 120 and 130 (or other shape or symbol segments) may be separated by at a segment of the housing 110 or another material placed between the logo portions. As described above, the insert portions 120 and 130 may define a portion of an electrical path that includes an electrical circuit within the housing 110 of the electronic device 100. In some embodiments, the electrical circuit may be a sensor. For example, the circuit may be a biometric sensor such as a fingerprint sensor. In such a case, when a user grasps the electronic device, the user's skin may come into contact with the insert portions 120 and 130 to complete an electrical path. In this manner, a user's fingerprint may be measured. It should be appreciated that the material inset into the insert portions 120, 130 may be conductive in order to facilitate an electrical connection to the sensor or other electrical contact or device positioned within or beneath the insert portions. Alternately, the material may be nonconductive to prevent direct coupling but still permit sensing therethrough. In still another embodiment, the edges of the cavities defining the logo portions (or other shape or symbol segments) may be electrically conductive, or may have an electrically conductive material deposited thereon. Thus, the edges of the various logo or symbol portions may define a conductive path between a user grasping the device, and specifically the portion of the user coming into contact with the edge in question, and the sensor, contact, or other electrical element positioned within, beneath or adjacent to the aperture.

In another example, the circuit may be a charging circuit for replenishing the charge of a battery within the electronic device 100. In such an embodiment, an external circuit may be required. For example, an external circuit may be a dock or a charging station with electrical contacts positioned and oriented to correspond to and interface with the insert portions 120 and 130. For example, the small insert portion 120 may be configured to receive a direct current power source and the large insert portion 130 may be configured to couple to ground. In this case, a power source may be configured to align with the small insert portion 120 when the electronic device 100 is docked. Similarly, a ground connector may be configured to align with the large insert portion 130. In this manner, a battery within the electronic device 100 may be recharged.

Figure 4:
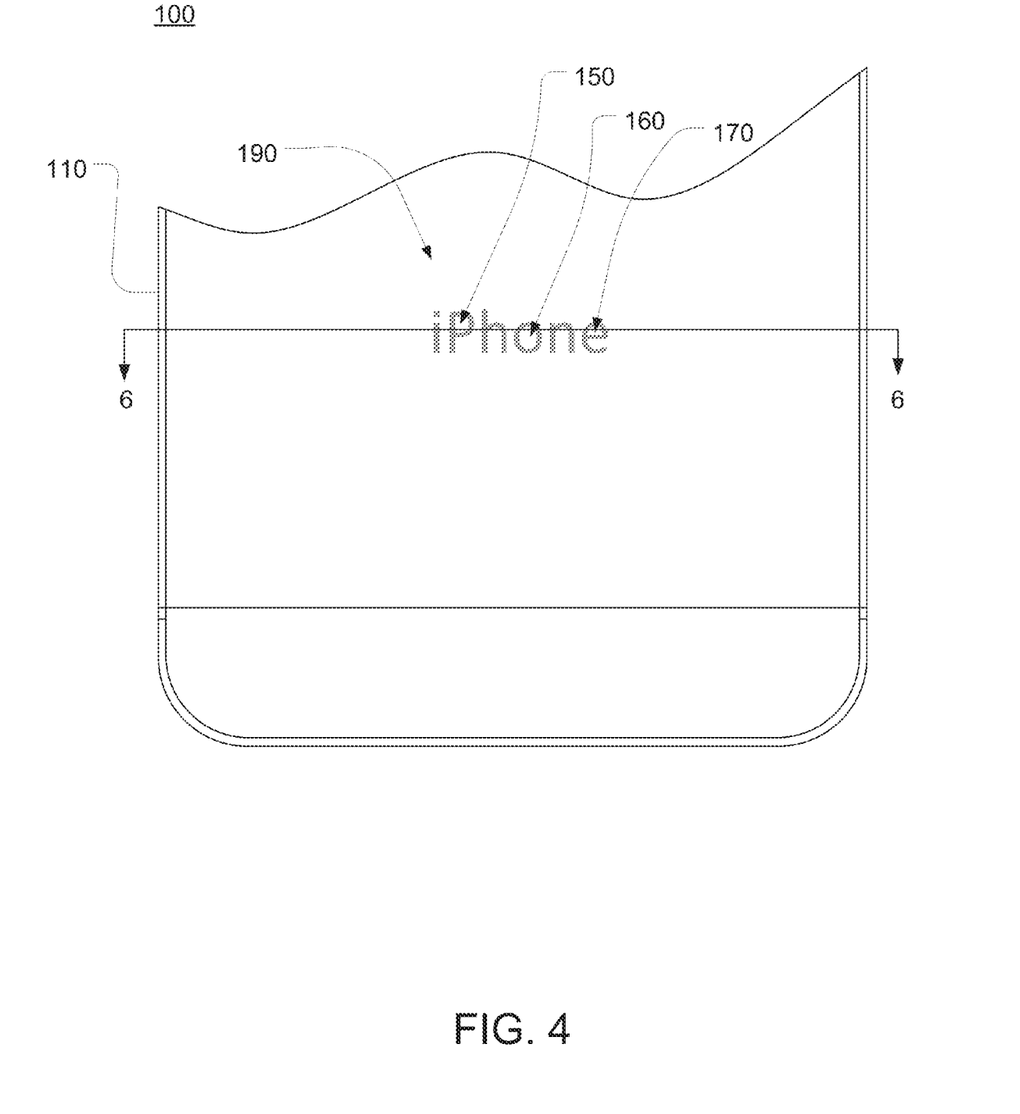
FIG. 4 depicts a second detailed view of a portion of the same electronic device as shown in FIG. 2.

FIG. 4 depicts a second detailed view of a portion of the same electronic device 100 as shown in FIG. 2. In this embodiment, the product identifier 190 may be a word with multiple letters. Depending upon the desired language or font, a word symbol may include one or more letters with a counter, or other fully enclosed portion. For example, in the illustrated embodiment, three counters 150, 160 and 170 are shown within the English letters P, o and e. In such an embodiment, the housing 110 may be entirely separated from the counter portions 150, 160, and 170. In this manner, the material chosen to form the lettering of the product identifier 190 may serve as an insulating boundary between the housing 110 and the counters 150, 160 and 170.

Figure 5:
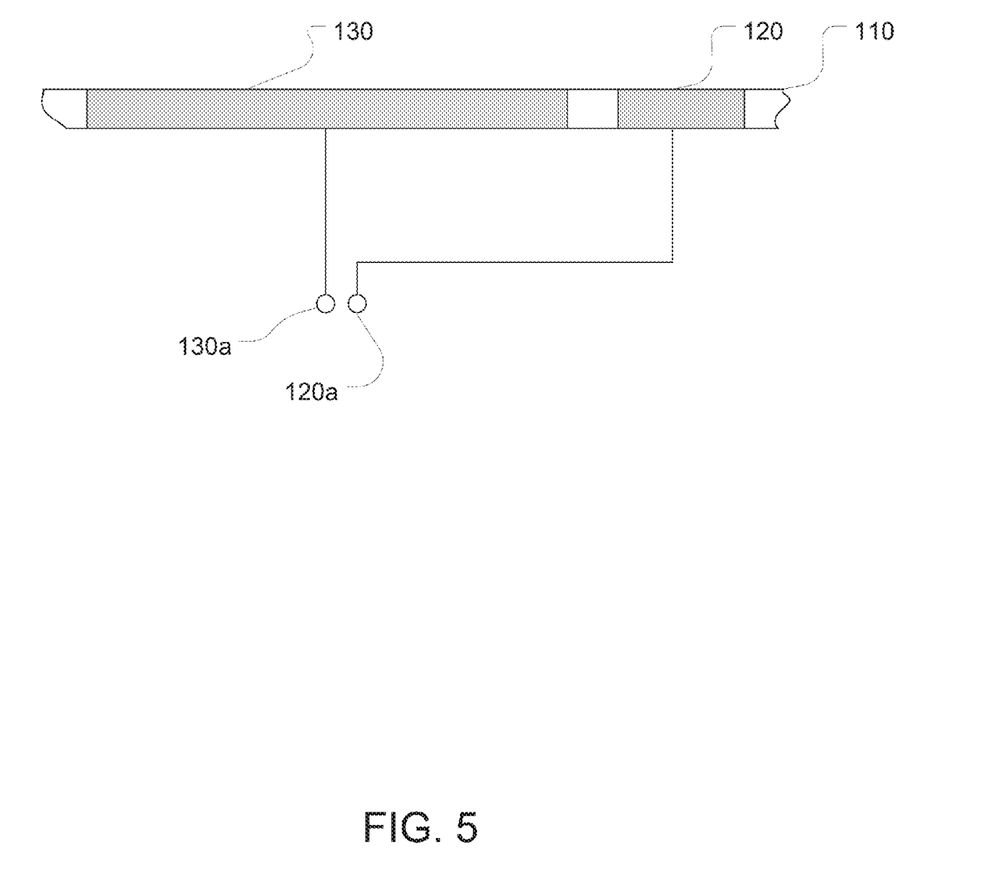
FIG. 5 depicts a cross-sectional view taken along line 5-5 of FIG. 3, showing a sample electrical contact concealed within a product logo.

FIG. 5 depicts a cross-sectional view taken along line 5-5 of FIG. 3, showing a sample electrical contact concealed within a product logo. In this cross section of the housing 110, the large insert portion 130 and small insert portion 120 are shown connecting to corresponding leads 130a and 120a. As described above, leads 120a and 130a may electrically couple to any suitable circuitry, such as charging circuitry or sensor circuitry. In this embodiment, the housing 110 may be constructed from an insulating material, such as plastic. In this way, the housing 110 may serve as an insulating boundary between the insert portions 120 and 130.

Figure 6:
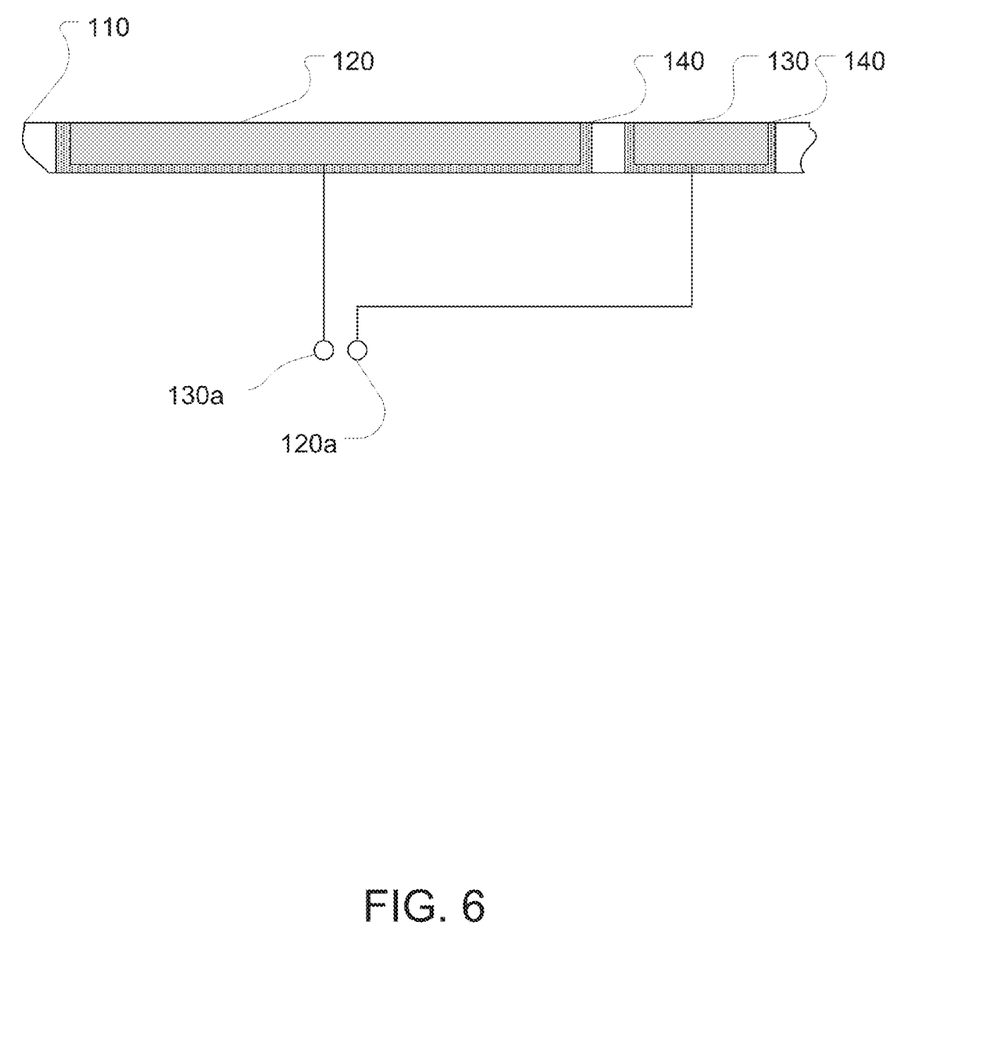
FIG. 6 depicts a cross-sectional view taken along line 5-5 of FIG. 3, showing an alternate sample electrical contact concealed within a product logo.

FIG. 6 depicts a cross-sectional view taken along line 5-5 of FIG. 3, showing a sample electrical contact concealed within a product logo. In this cross section of the housing 110, the large insert portion 130 and small insert portion 120 (each situated within different apertures defined within the housing) are shown connecting to corresponding leads 130a and 120a which may, in turn, electrically couple to any suitable circuitry, such as charging circuitry or sensor circuitry. In other embodiments, the leads may be omitted and the sensor or charging circuitry may directly couple to the aperture and/or insert portions. In still other embodiments, the insert portions 120, 130 may not couple to the circuitry or leads at all, but may simply shield them from the environment and/or direct contact while still permitting operation of the circuitry/leads through the material of the insert portions.

Also shown is insulating layer 140; insulating layer 140 may be composed of an electrically insulating material. For example, the insulating layer 140 may be rubber or plastic. In this embodiment, the material selected for the housing 110 may be conductive. For example, the housing 110 may be constructed of metal. The insulating layer 140 may act as an insulating boundary separating the housing 110 from the insert portions 120 and 130. This may be useful when the insert portions 120, 130 are electrically conductive and connected to the leads 120a, 130a. In some embodiments, the leads may likewise be electrically insulated from the housing.

Figure 7:
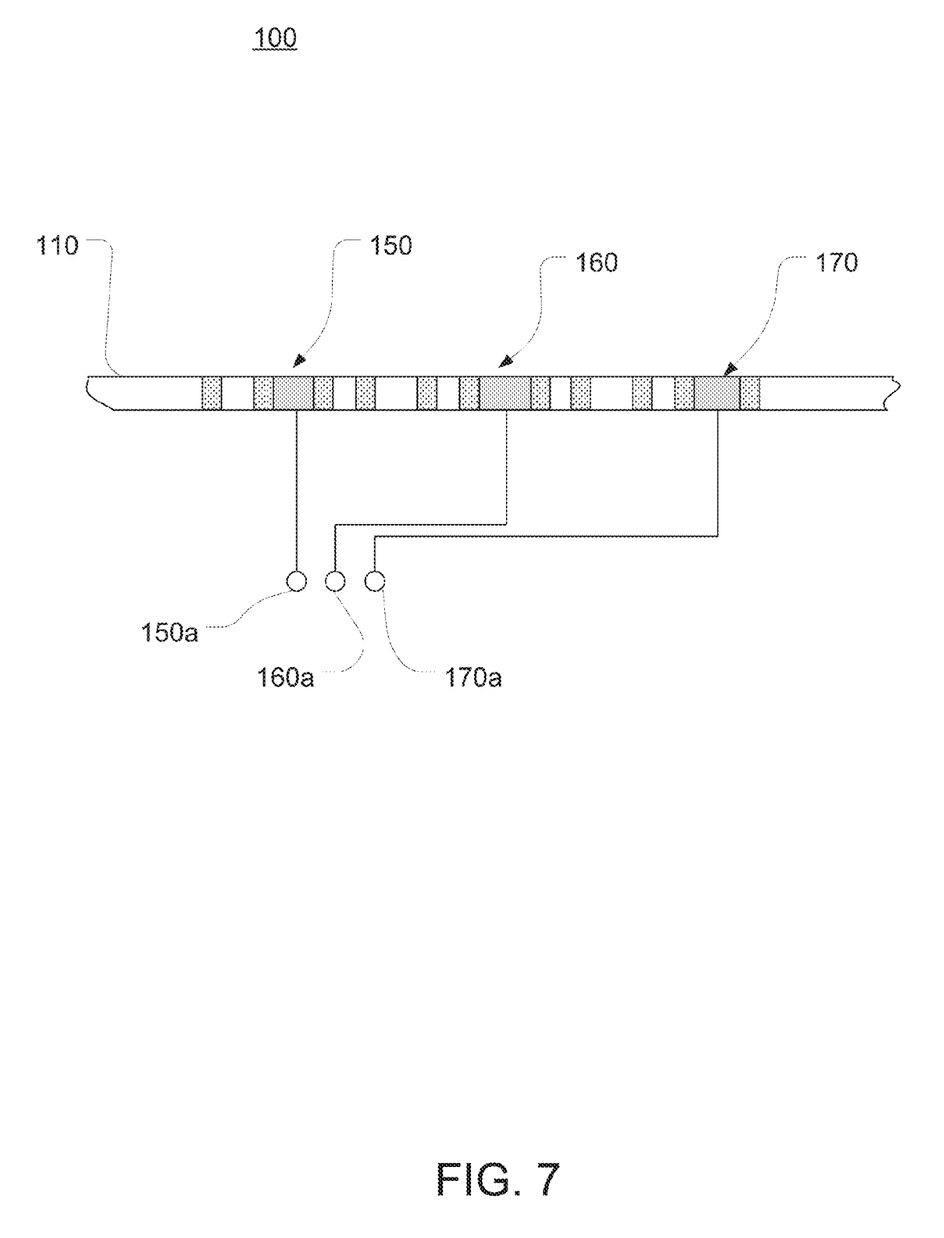
FIG. 7 depicts a cross-sectional view taken along line 6-6 of FIG. 4, showing an alternate sample electrical contact concealed within a product logo.

FIG. 7 depicts a cross-sectional view taken along line 6-6 of FIG. 4, showing an alternate sample electrical contact concealed within a product logo. In this cross section of the housing 110, the counter portions 150, 160 and 170 are shown connecting to corresponding leads 150a, 160a, and 170a respectively, although in some embodiments direct connections to a sensor or charger may be provided. As noted above, these leads may similarly connect or electrically couple to any suitable circuitry of the portable electronic device. Similar to FIG. 6, the embodiment shown in FIG. 7 may optionally include an insulating layer (not shown). Alternately, the embodiment shown in FIG. 7 may include individual leads coupled to each of the several letters of the word or words selected as the product identifier 190. In such an embodiment, the counter portions 150, 160 and 170 may or may not also be coupled to corresponding leads.

The number of leads and the layout, orientation, and positioning of the various individual portions of a product identifier 190 may vary from embodiment to embodiment. Further, the number of leads may also directly relate to the number of sensors which may be coupled to those leads. For example, multiple sensors may be operated simultaneously in an embodiment enjoying a plurality of leads. Alternately, a single pair of leads and corresponding contacts may enjoy varied functionality from time to time. For example, in a first mode a pair of contacts may be operated as a portion of a sensor circuit. In a second mode, the same pair of contacts may be operated as a portion of a charging circuit.

Although the disclosure above is described in terms of various exemplary embodiments and implementations, it should be understood that the various features, aspects and functionality described in one or more of the individual embodiments are not limited in their applicability to the particular embodiment with which they are described, but instead can be applied, alone or in various combinations, to one or more of the other embodiments of the invention, whether or not such embodiments are described and whether or not such features are presented as being a part of a described embodiment. Thus, the breadth and scope of the present invention should not be limited by any of the above-described exemplary embodiments but is instead defined by the claims herein presented.

I claim:
1. A portable electronic device comprising:
  a housing;
  an aperture defined by the housing; and
  a visually opaque insert positioned within the aperture and forming at least a portion of an externally visible symbol; and
  an electromagnetic wave sensor positioned beneath or within the visually opaque insert, the electromagnetic wave sensor operative to sense a health parameter of a person in contact with the visually opaque insert.

2. The portable electronic device of claim 1, wherein the aperture is a first aperture the electromagnetic wave sensor is a first electromagnetic wave sensor and the visually opaque insert is a first insert and wherein the portable electronic device further comprises:
a second aperture defined by the housing;
a second insert positioned within the second aperture; and
a second electromagnetic wave sensor positioned beneath or within the first insert, the second electromagnetic wave sensor operative to cooperate with the first electromagnetic wave sensor to sense the health parameter.

3. The portable electronic device of claim 2, wherein:
the first and second apertures are first and second portions of the externally visible symbol.

4. The portable electronic device of claim 3, wherein:
the externally visible symbol comprises at least a portion of a word;
the first portion of the externally visible symbol comprises at least a portion of a first letter of the word; and
the second portion of the externally visible symbol comprises at least a portion of a second letter of the word.

5. The portable electronic device of claim 1, wherein the electromagnetic wave sensor comprises an infrared sensor.

6. The portable electronic device of claim 1, further comprising a touch screen.

7. The portable electronic device of claim 3, wherein the first insert and the second insert at least partially define an electrical path operative with a battery charging circuit.

8. The portable electronic device of claim 3, wherein the first insert has a larger surface area than the second insert.

9. The portable electronic device of claim 3, wherein the first insert and the second insert are electrically insulated from the housing.

10. A portable electronic device comprising:
a rigid housing comprising:
an external surface
a first insert at least partially defining a first portion of a symbol within the external surface; and
a second insert at least partially defining a second portion of the symbol; and
a sensor configured to sense radio frequency or infrared waves passing through one or both of the first and second inserts.

11. The portable electronic device of claim 10, wherein the symbol comprises at least a portion of a product logo.

12. The portable electronic device of claim 10, wherein the symbol comprises at least a portion of a glyph.

13. The portable electronic device of claim 10, wherein the sensor is in electrical contact with at least one of the first insert and the second insert.

14. The portable electronic device of claim 10, wherein the first insert and the second insert at least partially define an electrical path for charging a battery within the housing.

15. The portable electronic device of claim 10, wherein the first insert of the housing comprises:
an aperture defined in the housing; and
an insert material positioned within the aperture; wherein at least one of the insert material and the housing is electrically conductive.

16. The portable electronic device of claim 15, wherein:
the insert material is electrically conductive; and
the insert material defines an electrical path between a sensor contiguous with the insert material and an exterior of the insert material.

17. The portable electronic device of claim 15, wherein:
the insert material is electrically nonconductive; and
an electrical path is defined by an edge of the aperture, the electrical path electrically connecting a sensor within the housing to an exterior of the housing.

18. The portable electronic device of claim 10, wherein the first insert and the second insert at least partially define an electrical path comprising a battery charging circuit.

19. A portable electronic device, comprising:
a housing;
an aperture defined by the housing; and
a visually opaque insert positioned within the aperture and forming at least a portion of an externally visible symbol; and
an infrared sensor positioned beneath the visually opaque insert, the infrared sensor operative to sense infrared waves passing through the visually opaque insert.

20. The portable electronic device as recited in claim 19, wherein the housing defines multiple apertures, a visually opaque insert being positioned within each of the multiple apertures, wherein each of the visually opaque inserts is transparent to infrared waves, allowing infrared waves to pass through the visually opaque inserts and be sensed by the infrared sensor.

* * * * *

UNITED STATES PATENT AND TRADEMARK OFFICE
CERTIFICATE OF CORRECTION

PATENT NO. : 9,593,969 B2
APPLICATION NO. : 14/142641
DATED : March 14, 2017
INVENTOR(S) : Nicholas V. King It is certified that error appears in the above-identified patent and that said Letters Patent is hereby corrected as shown below:

Claim 10, Line 3 (Column 7, Line 47): Insert --,-- after the word surface

Claim 15, Line 4 (Column 8, Line 14): Delete ";" and insert --,-- after the word aperture Signed and Sealed this
Third Day of April, 2018

Andrei Iancu
*Director of the United States Patent and Trademark Office*